United States Patent
Olschewski (10) Patent No.: US 7,319,520 B2
(45) Date of Patent: Jan. 15, 2008

(54) METHOD FOR SEPARATING FLUORESCENCE SPECTRA OF DYES PRESENT IN A SAMPLE

(75) Inventor: Frank Olschewski, Heidelberg (DE)

(73) Assignee: Leica Microsystems CMS GmbH, Wetzlar (DE)

(*) Notice: Subject to any disclaimer, the term of this patent is extended or adjusted under 35 U.S.C. 154(b) by 274 days.

(21) Appl. No.: 10/924,422

(22) Filed: Aug. 24, 2004

(65) Prior Publication Data

US 2005/0046836 A1 Mar. 3, 2005

(30) Foreign Application Priority Data

Aug. 27, 2003 (DE) ............... 103 39 311

(51) Int. Cl.
- G06F 7/16 (2006.01)
- G01J 3/30 (2006.01)
- G01J 3/433 (2006.01)
- G01J 3/14 (2006.01)
- G01J 3/18 (2006.01)

(52) U.S. Cl. .............. 356/329; 356/317; 356/318; 356/332; 703/2

(58) Field of Classification Search ........... 356/326, 356/329, 317, 318, 331–334; 703/2; 702/30–32
See application file for complete search history.

(56) References Cited

U.S. PATENT DOCUMENTS

| | | | |
|---|---|---|---|
| 3,720,822 A | | 3/1973 | Rochester et al. |
| 5,303,026 A | * | 4/1994 | Strobl et al. ............ 356/318 |
| 5,591,981 A | * | 1/1997 | Heffelfinger et al. .... 250/458.1 |
| 5,813,987 A | * | 9/1998 | Modell et al. ............ 600/473 |
| 5,828,452 A | * | 10/1998 | Gillispie et al. ............ 356/328 |
| 5,886,784 A | * | 3/1999 | Engelhardt ................ 356/326 |
| 6,069,689 A | * | 5/2000 | Zeng et al. .................. 356/73 |
| 6,097,870 A | | 8/2000 | Ranka et al. |

(Continued)

FOREIGN PATENT DOCUMENTS

DE 19829944 A1 1/2000

(Continued)

OTHER PUBLICATIONS

Warner, I.M., Christian, G.D, Davidson, E.R., Callis, J.B., "Analysis of multicomponent fluorescence data," Analytical Chemistry (1977), 49(4), 564-73.*

(Continued)

*Primary Examiner*—Gregory J. Toatley, Jr.
*Assistant Examiner*—Bryan J Giglio
(74) *Attorney, Agent, or Firm*—Houston Eliseeva LLP (57) ABSTRACT

A system and a method for setting a fluorescence spectrum measurement system for microscopy is disclosed. Using illuminating light (3) from at least one laser that emits light of one wavelength, a continuous wavelength region is generated. Dyes are stored, with the pertinent excitation and emission spectra, in a database of a computer system (23). For each dye present in the specimen (15), a band of the illuminating light (3) and a band of the detected light (17) are calculated, the excitation and emission spectra read out from the database being employed. Setting of the calculated band in the illuminating light and in the detected light is performed on the basis of the calculation. Lastly, data acquisition is accomplished with the spectral microscope (100).

22 Claims, 7 Drawing Sheets

U.S. PATENT DOCUMENTS

| | | | | |
|---|---|---|---|---|
| 6,166,804 | A * | 12/2000 | Potyrailo et al. | 356/318 |
| 6,300,639 | B1 | 10/2001 | Wiederhoeft | |
| 6,556,236 | B1 * | 4/2003 | Swift et al. | 348/56 |
| 6,571,118 | B1 * | 5/2003 | Utzinger et al. | 600/476 |
| 6,584,413 | B1 * | 6/2003 | Keenan et al. | 702/28 |
| 6,690,817 | B1 * | 2/2004 | Cabib et al. | 382/134 |
| 6,738,502 | B1 * | 5/2004 | Coleman et al. | 382/133 |
| 6,766,184 | B2 * | 7/2004 | Utzinger et al. | 600/407 |
| 6,825,928 | B2 * | 11/2004 | Liu et al. | 356/317 |
| 6,870,613 | B1 * | 3/2005 | Tisone et al. | 356/317 |
| 2001/0041843 | A1 * | 11/2001 | Modell et al. | 600/473 |
| 2003/0030801 | A1 * | 2/2003 | Levenson et al. | 356/326 |
| 2003/0155494 | A1 | 8/2003 | Olschewski | |
| 2004/0036763 | A1 * | 2/2004 | Swift et al. | 348/51 |
| 2006/0007439 | A1 * | 1/2006 | Corcoran | 356/317 |

FOREIGN PATENT DOCUMENTS

| | | |
|---|---|---|
| DE | 100 06 800 | 8/2001 |
| DE | 10206979 A1 | 8/2003 |
| DE | 102 27 111 | 12/2003 |

OTHER PUBLICATIONS

Warner, I.M., Christian, G.D, Davidson, E.R., "Quantitative analyses of multicomponent fluorescence data by the methods of least squares and non-negative least sum of errors", Analytical Chemistry (1977), 49(14), 2155-9.*

Vives, MI., Gargallo, R., Tauler, R., "Three-Way Multivariate Curve Resolution Applied to Speciation of Acid-Base and Thermal Unfolding Transaction of an Alternating Polynucleotide", Biopolymers, vol. 59, 477-488 (2001).*

* cited by examiner

METHOD FOR SEPARATING FLUORESCENCE SPECTRA OF DYES PRESENT IN A SAMPLE

RELATED APPLICATIONS

This application claims priority of the German patent application 103 39 311.0.

FIELD OF THE INVENTION

The invention concerns a system for illumination and for the detection of fluorescence signals. The invention further concerns a spectral microscope.

The invention furthermore discloses a method for determining illumination and detection parameters for the sensing of fluorescence processes. The invention further concerns a method for data acquisition using a spectral microscope.

BACKGROUND OF THE INVENTION

U.S. Pat. No. 6,097,870 discloses an arrangement for generating a broadband spectrum in the visible and infrared spectral region. The arrangement is based on a microstructured fiber into which the light of a pump laser is coupled. In the microstructured fiber, the pump light is broadened by nonlinear effects. So-called photonic band-gap material or photon crystal fibers, or "holey" fibers, are also used as microstructured fibers. Embodiments as so-called "hollow fibers" are also known.

Arc lamps are known as broadband light sources, and are used in many sectors. U.S. Pat. No. 3,720,822 "Xenon photography light," which discloses a xenon arc lamp for illumination in photography, may be cited here as an example.

German Patent Application DE 100 06 800.6 discloses an apparatus for selection and detection of at least one spectral region of a spectrally spread light beam (SP module). Selection means that are embodied as sliders are provided in the spread-out beam of the light coming from the specimen to be examined, in order thereby to direct portions of the spread-out light beam to various detectors. The signals of the detectors are then used for image generation. DE 100 06 800.6 does not disclose actuation of the sliders so as to enable rapid and reliable detection of a specific spectrum.

U.S. Pat. No. 5,791,024 discloses a method for classifying chromosomes. In the detection of chromosome defects, the chromosomes are provided with five different fluorescing dyes. Based on the attachment of the dyes to the chromosomes, the latter can be unequivocally classified. From a comparison with a reference, conclusions can be drawn as to the genetic defects that are present. An unequivocal determination is possible because the chromosome emits a characteristic spectrum as a result of the dyes attached to that chromosome. The method presented here is suitable in particular for determining the spectra of the individual chromosomes, but cannot be applied to fluorescence measurements using a scanning microscope.

DE 102 27 111.9 discloses a spectral microscope and a method for data acquisition using a spectral microscope. Methods and systems for sensing maximum information from a fluorescing microscopic specimen are encompassed. Optimum information acquisition is not, however, possible with this method.

SUMMARY OF THE INVENTION

It is the object of the invention to create a method for acquiring optimum color information from a fluorescing microscopic specimen or a specimen provided with fluorescing markers.

The aforesaid object is achieved by way of a method for setting a spectral scanning microscope, comprising the following steps:
a) generating an illuminating light from at least one laser that emits light of one wavelength, the generated illuminating light encompassing a discrete wavelength region;
b) transmitting the at least one dye present in the specimen to a computer system and reading out the pertinent excitation and emission spectra stored in a database;
c) calculating a band of the illuminating light for each dye present in the specimen and calculating a band of the detected light for each dye present in the specimen, the excitation and emission spectra read out from the database being employed;
d) setting the calculated band in the illuminating light and setting the calculated detection band; and
e) performing data acquisition with the spectral scanning microscope.

The object is as well achieved by a method for setting a spectral scanning microscope, comprising the following steps:
a) generating an illuminating light from at least one laser that emits light of one wavelength, the generated illuminating light encompassing a continuous wavelength region;
b) transmitting the at least one dye present in the specimen to a computer system and reading out the pertinent excitation and emission spectra stored in a database;
c) calculating a band of the illuminating light for each dye present in the specimen and calculating a band of the detected light for each dye present in the specimen, the excitation and emission spectra read out from the database being employed;
d) setting the calculated band in the illuminating light and setting the calculated detection band; and
e) performing data acquisition with the spectral microscope.

A further object of the invention is to create a method that makes possible the acquisition of optimum color information from a fluorescing microscopic specimen.

The aforesaid object is achieved by way of a system for setting a fluorescence spectrum measurement system for microscopy, comprises: a laser emitting light, an illumination system that generates a continuous wavelength region from the light of the laser and defines an illuminating light, a Spectral Photometer, hereinafter an SP module, that receives a detected light proceeding from a specimen, an optical deflection means that is provided in the illuminating light and in the detected light, a computer system with a database in which multiple excitation and emission spectra of dyes are stored; a means for calculating a band of the illuminating light for each dye present in the specimen and for calculating a band of the detected light for each dye present in the specimen is implemented in the computer system, wherein the excitation and emission spectra present in the database of the computer system being used; and means for setting the calculated band in the illuminating light and means for setting the calculated band in the detected light.

The method has the advantage that firstly an illuminating light is generated from at least one laser that emits light of one wavelength, the generated illuminating light encompassing a continuous wavelength region. The dyes present in the specimen are communicated to a computer system, and the pertinent excitation and emission spectra, stored in a database, are read out from the database for further calculations. A band of the illuminating light is calculated for each dye present in the specimen. A band of the detected light is likewise calculated for each dye present in the specimen. The excitation and emission spectra read out from the database are employed for calculation.

The system for setting a fluorescence spectrum measurement system for microscopy encompasses an illumination system that, from the light of a laser, generates a continuous wavelength region and defines an illuminating light. Also provided is an SP module that receives a detected light proceeding from a specimen. Also provided is an optical deflection means that is provided both in the illuminating light and in the detected light. A computer system encompasses a database in which multiple excitation and emission spectra of dyes are stored. The computer system possesses a means for calculating a band of the illuminating light for each dye present in the specimen, and for calculating a band of the detected light for each dye present in the specimen, the calculation being performed from the standpoint of achieving an optimum information yield. Means for setting the calculated band in the illuminating light, and means for setting the calculated band in the detected light, are present.

Setting can be accomplished automatically. Calculation of the band in the illuminating light and the detected band is accomplished by modeling and optimizing the optical configuration of the spectral microscope, at least one boundary condition to be defined by the user being employed. The band of the illuminating light is set by way of an Acousto-Optical Beam Splitter, hereinafter an AOBS. The band of the detected light is set by means of an SP module.

Upon detection, a spectral intensity vector $I^{Det}$, which is made up of a linear combination of the emission spectra $s_i^{em}$ of the dyes introduced into the specimen, is detected for each pixel. Likewise for excitation, a spectral intensity vector $I^{Ex}$, which is made up of a linear combination of the excitation spectra $s_i^{ex}$ of the dyes introduced into the specimen, is generated for each pixel.

BRIEF DESCRIPTION OF THE DRAWINGS

The subject matter of the invention is depicted schematically in the drawings and will be described below with reference to the Figures, in which.

DETAILED DESCRIPTION OF THE INVENTION

Figure 1:
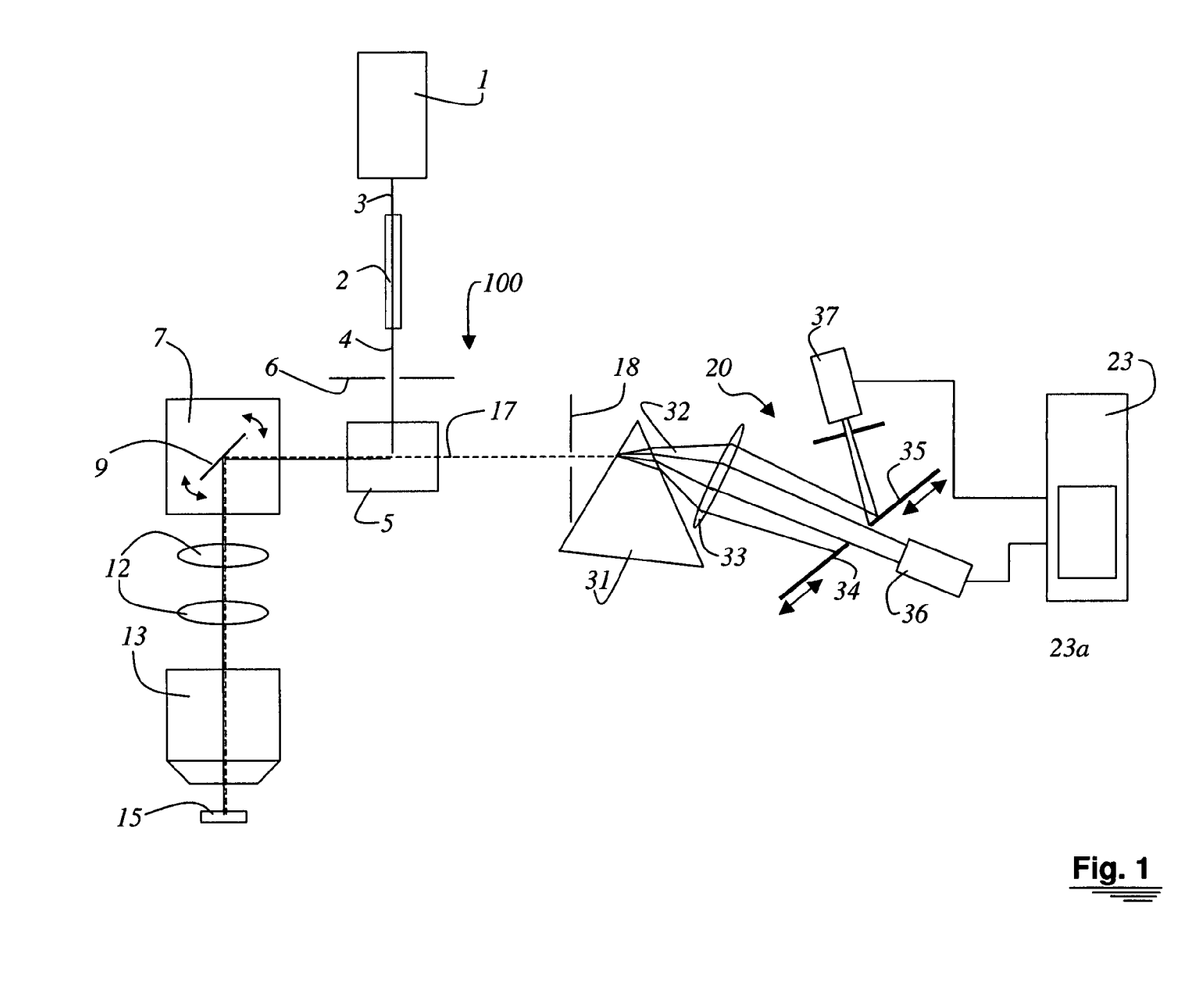
FIG. 1 schematically depicts a scanning microscope, the detector being preceded by an SP module.

FIG. 1 schematically shows the exemplary embodiment of a confocal scanning microscope 100. This is not, however, to be construed as a limitation of the invention, and one skilled in the art is well aware that the same invention-relevant components can also be installed in fluorometers, cytometers, and microscope systems of different design. Illuminating light 3 coming from at least one illumination system 1 is directed by a beam splitter or a suitable deflection means 5 to a scanning module 7. Before illuminating light 3 encounters deflection means 5, it passes through an illumination pinhole 6. Scanning module 7 encompasses a gimbal-mounted scanning mirror 9 that guides illuminating light 3 through a scanning optical system 12 and a microscope optical system 13 and over or through a specimen 15. A light guiding fiber or a micro structured optical element 2 can be configured in such a way that it generates white light from the light of a laser (the laser is illumination system 1). The deflection means 5 separates from the white-light spectrum a sub-band or a continuous wavelength region and conveys it further. A micro structured element 2 or a tapered glass fiber is provided for this purpose. (The assemblage for the generation of white light is described in more detail in FIG. 3.) In the case of non-transparent specimens 15, illuminating light 3 is guided over the specimen surface. With biological specimens 15 (preparations) or transparent specimens, illuminating light 3 can also be guided through specimen 15. For that purpose, non-luminous preparations are optionally prepared with a suitable dye (not shown, since this is established existing art). The dyes present in specimen 15 are excited by illuminating light 3 and emit light in a characteristic region of the spectrum peculiar to them. This light proceeding from specimen 15 is a detected light 17. It travels through microscope optical system 13 and scanning optical system 12 and via scanning module 7 to deflection means 5, traverses the latter, and arrives via a detection pinhole 18 at at least one detector 36, 37 which is embodied as a photomultiplier. It is clear to one skilled in the art that other detection components, for example diodes, diode arrays, photomultiplier arrays, CCD chips, or CMOS image sensors, can also be used. Detected light 17 proceeding from or defined by specimen 15 is depicted in FIG. 1 as a dashed line. In detectors 36, 37, electrical detected signals proportional to the power level of the light proceeding from specimen 15 are generated. Because, as already mentioned above, light having a characteristic spectrum is emitted from specimen 15, it is useful to provide an SP module 20 in front of the at least one detector 36, 37. The data generated by the at least one detector 36, 37 are conveyed to a computer system 23. At least one peripheral device is associated with computer system 23. The peripheral device can be, for example, a display on which the user receives instructions for setting scanning microscope 100 or can view the current setup as well as the image data in graphical form. Also associated with computer system 23 is an input means that comprises, for example, a keyboard, a setting apparatus for the components of the microscope system, and a mouse.

SP module 20 (FIG. 2) is embodied in such a way that it can acquire a complete lambda scan, i.e. all the wavelengths proceeding from specimen 15 are recorded. The data are transferred to computer system 23 and can then be presented on display 27 in a manner definable by the user. Detected light 17 is spatially spectrally divided using a prism 31. A further possibility for spectral division is the use of a reflection or transmission grating. Spectrally divided light fan 32 is focused with focusing optical system 33 and then strikes a mirror stop arrangement 34, 35. Mirror stop arrangement 34, 35, the means for spectral spatial division, focusing optical system 33, and detectors 36 and 37 are together referred to as the SP module (or multi-band detector) 20.

Figure 2:
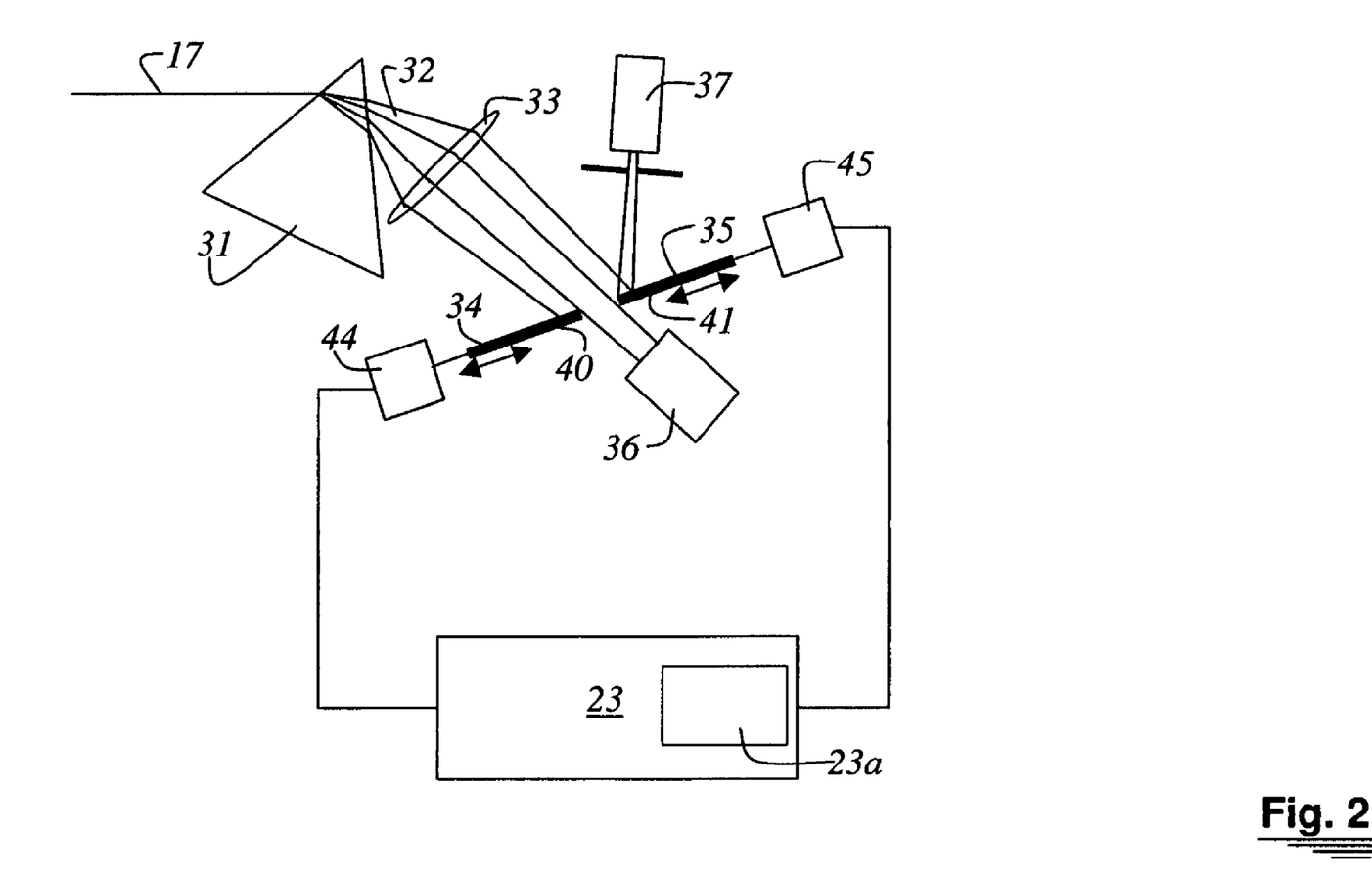
FIG. 2 schematically depicts the SP module in detail.

As is evident from FIG. 2, a desired portion of the spectrum of detected light 17 can be picked out or systematically selected by means of mirror stop arrangement 34, 35. In the exemplary embodiment depicted here, slit aperture arrangement 34, 35 is equipped with a first and a second slider 40 and 41. It is self-evident that for the selection of more than two spectral regions, a corresponding number of sliders must be provided. A corresponding increase in the mirror sliders results directly in an increase in the spectral bands acquired concurrently. A first motor 44 is associated with first slider 40, and a second motor 45 with second slider 41. Motors 44 and 45 permit a displacement of sliders 40 and 41 that is described in accordance with the method below. As a result of the displacement of sliders 40 and 41, only a portion of divided light fan 32 of detected light 17, containing only light of the preselected spectral region, passes through mirror stop arrangement 34, 35 and is detected by detector 36, which is embodied as a photomultiplier. Another portion of divided light fan 32 is reflected at mirror stop arrangement 35 and travels to detector 37, which is likewise embodied as a photomultiplier.

Figure 3:
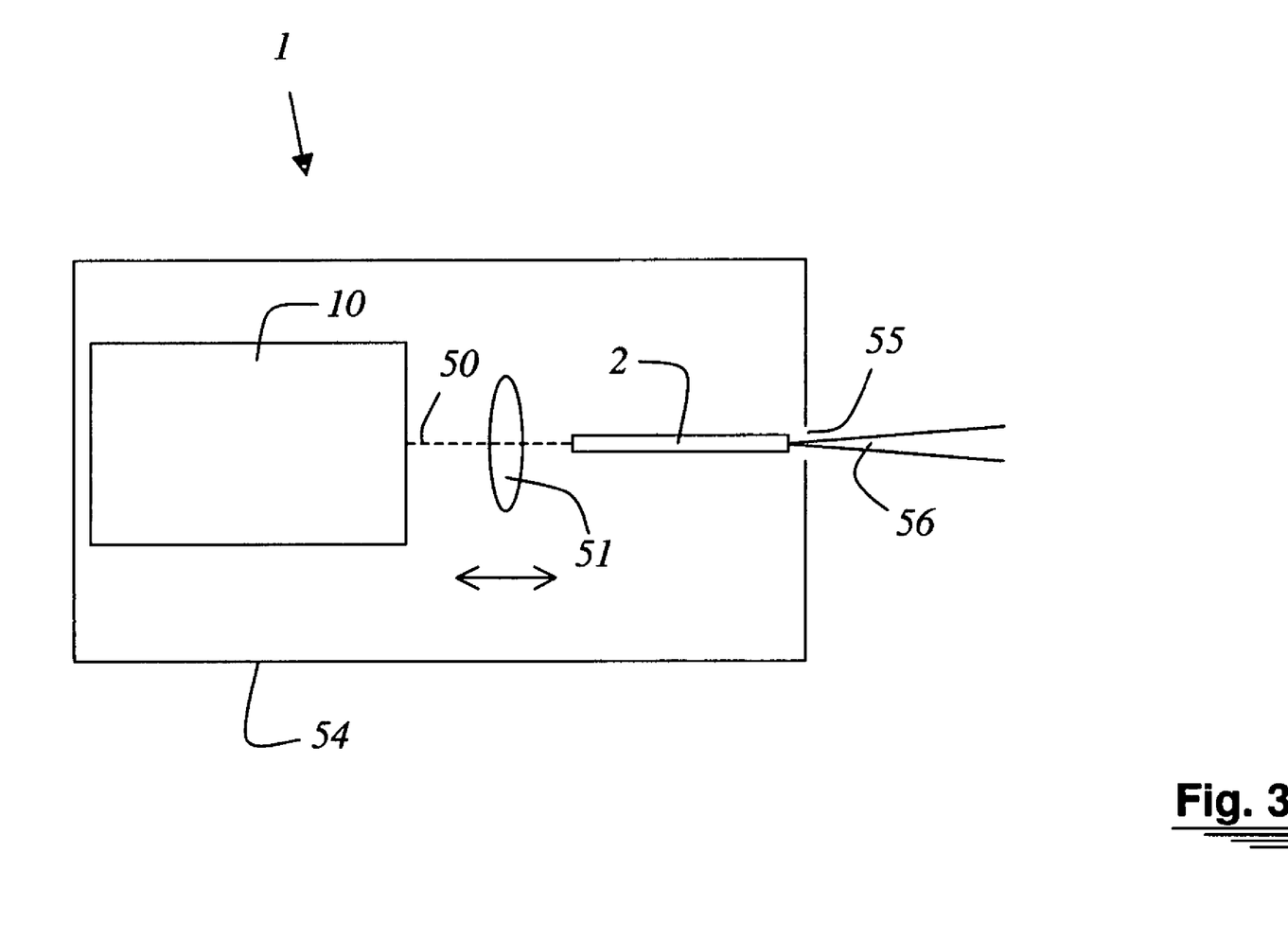
FIG. 3 shows an illumination system for a scanning microscope according to the present invention.

FIG. 3 shows illumination system 1, which contains a laser 10 that is embodied as a diode-laser-pumped, mode-coupled Ti:sapphire laser and emits a pulsed light beam 50 (corresponding to the illuminating light beam of FIG. 1) that is drawn as a dashed line. The duration of the light pulses is approx. 100 fs at a repetition rate of approx. 80 MHz. Light beam 50 is focused, with focusing optical system 51 that is configured as a zoom optical system and is arranged displaceably along the propagation direction of the light beam, onto a microstructured optical element 2 that comprises a crystal of photonic band-gap material. In microstructured optical element 2, the light of laser 10 is spectrally broadened. All the components are located in a housing 54 having a light exit opening 55 through which spectrally broadened light 56 leaves the housing as a divergently proceeding beam. The spectrum of spectrally broadened light 56 extends from approx. 300 nm to 1600 nm, the light power level being largely constant over the entire spectrum. In one exemplary embodiment, microstructured optical element 2 can also comprise a light guide that is given a cross-sectional taper. The emitted light of laser 10 is spectrally broadened in the light guide. Illuminating light 3 (see FIG. 1) travels to deflection means 5, which is configured front an acoustooptical element. The acoustooptical element is embodied as an acoustooptical tunable filter (AOTF) which, for investigation of the specimen, reduces illuminating light 3 in accordance with a user-selected band extending from 1-2.

Figure 4:
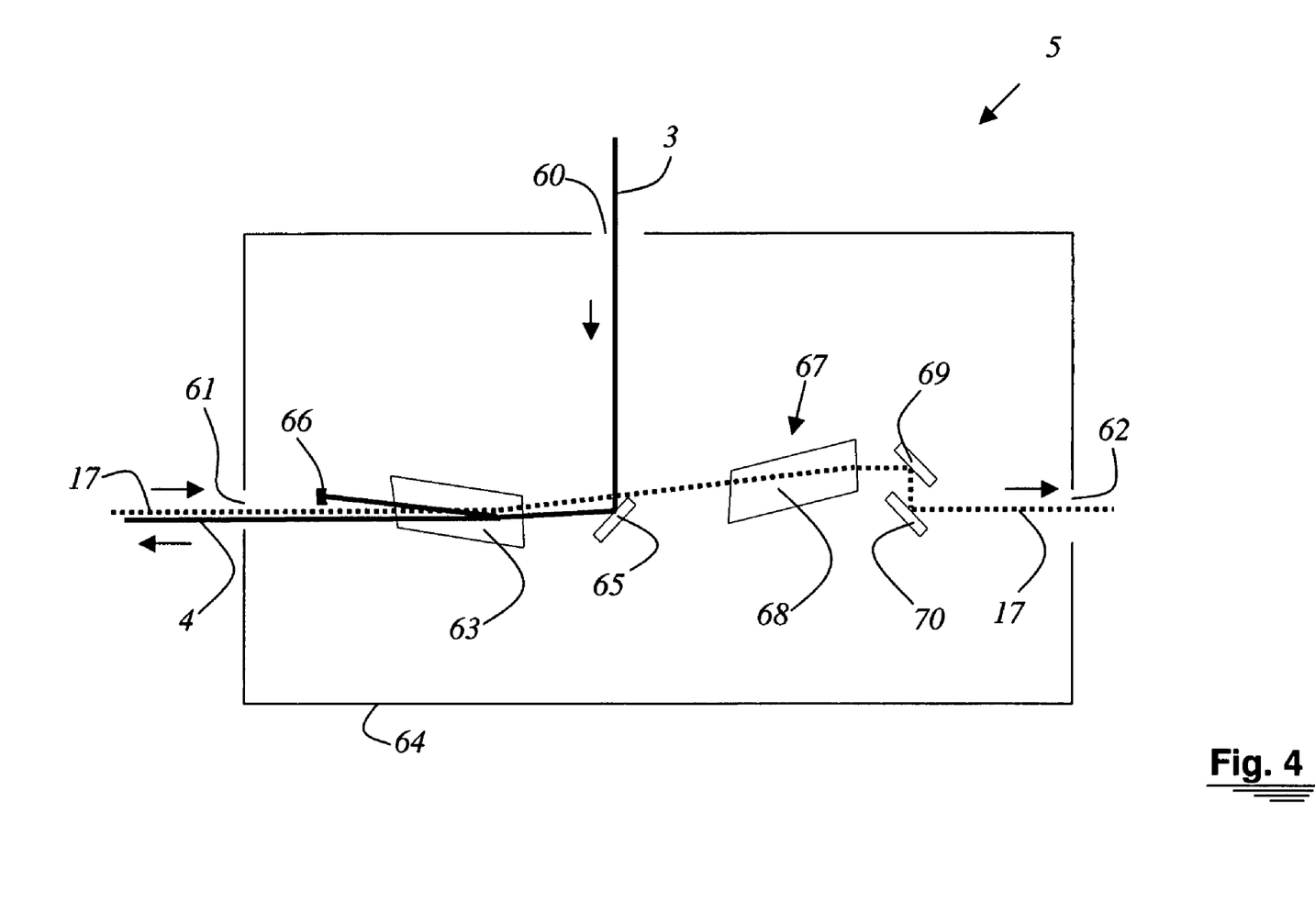
FIG. 4 shows an embodiment of an optical element that is provided for directing the illuminating light beam and the detected light beam.

FIG. 4 shows, in detail, optical deflection means 5 that is placed in front of SP module 20. Optical deflection means 5 comprises a first port 60, a second port 61, and a third port 62, illuminating light 3 being coupled into first port 60. At second port 61, illuminating light 3 is coupled out and detected light 17 is coupled in. At third port 62, the detected light beam is coupled out and conveyed to SP module 20. Optical deflection means 5 contains a first acoustooptical component 63 and is configured as an exchangeable module with a housing 64. The incoming illuminating light 3 is directed by a deflection mirror 65 onto first acoustooptical component 63. Acoustooptical component 63 is embodied as an AOTF that is traversed by an acoustic wave. The acoustic wave is generated by an electrically activated piezoacoustic generator. The frequency of the acoustic wave is selected in such a way that only those portions of illuminating light 3 having the desired wavelength are directed toward second port 61. The other portions of illuminating light 3, not influenced by the acoustic excitation, are directed into a beam trap 66. The power level of illuminating light 3 emerging from second port 61 can be selected by varying the amplitude of the acoustic wave; this is particularly advantageous especially for reflection-microscopy applications. The crystal sectioning and orientation of acoustooptical component 63 are selected in such a way that with the same incoupling direction, different wavelengths are deflected in the same direction.

Optical element 5 makes it possible to vary the power level of illuminating light 3, to vary the power level of at least one selectable wavelength or at least one selectable wavelength band of illuminating light 3, and also to completely block out selectable wavelengths or selectable wavelength bands. Detected light 17, which is depicted with dashed lines in FIGS. 2 and 4, strikes first acoustooptical component 63 in a propagation direction opposite to that of illuminating light 3. The portions of detected light 17 having the same wavelength and polarization as illuminating light 3 are directed completely or partially (depending on the amplitude of the acoustic wave) onto deflection mirror 65 and then to first port 60; with a diminished amplitude, the uninfluenced portion travels past deflection mirror 65. If detected light 17 is, for example, reflected light, optical element 5 then acts as a variable neutral beam splitter whose splitting ratio is determined by the amplitude of the acoustic wave. If detected light 17 is fluorescent light whose wavelength is modified, for example, as a result of Stokes or Raman shifting, it is not influenced by the acoustic wave and travels past deflection mirror 65. Because of the double refraction of first acoustooptical component 63, detected light 17 is split into an ordinarily polarized and an extraordinarily polarized beam. In addition, the ordinarily and extraordinarily polarized beams are each also spectrally spread out as a result of the prismatic effect of acoustooptical component 63. An optical compensation element 67 comprising a further acoustooptical component 68 is provided for compensation. Further acoustooptical component 68 corresponds in configuration to first acoustooptical component 63. It is arranged rotated 180 degrees about the beam axis with respect to first acoustooptical component 63. The spread-out sub-beams having differing polarization directions are thereby recombined. At the same time, the spectral spreading of first acoustooptical component 63 is annulled. A slight parallel offset does, however, remain for detected light of different wavelengths. After passing through further acoustooptical component 67, detected light 17 strikes a mirror pair that is made up of a first mirror 69 and a second mirror 70. The mirror pair serves to bring detected light 17 into the desired beam axis, namely the beam axis exhibited by detected light 17 entering through second port 61. This simplifies the exchangeability of optical deflection means 5 with an element having a conventional beam splitter. Just like illuminating light 3, detected light 17 can be varied as to power level, in spectrally selective fashion, using first acoustooptical component 63 or also using further acoustooptical component 63. The acoustically injected waves are subsequently used as control signals.

In the description hereinafter, the spectra are mathematically coded as vectors, the components of the vector corresponding in each case to the value in a specific spectral band. One element of the vector thus corresponds to one individual measurement of a channel using SP module 20. When a spectral microscope or microscope as described, for example, in FIG. 1 is used for color imaging, it then detects for each pixel a spectral intensity vector $I^{Det}$ that can be represented, as follows $$I^{Det} = \sum_i c_i s_i^{em} = M_{Det} c, \qquad (1)$$

as a linear combination of known emission spectra $s_i^{em}$. One pixel is the result, for example, of single-point illumination by the scanning laser beam. If a CCD detector, for example, is used to detect the light proceeding from the specimen, the cells of the detector are then the individual pixels. The components of the intensity vector correspond to the intensity detected in the microscope's detectors or to a time-gated count signal proportional to the number of photons; optionally, these are individually amplified by means of individual amplifiers (a detail that is ignored hereinafter for reasons of simplicity and can be embedded into the matrix as a correction component at any time by the skilled mathematician). The emission spectra $s_i^{em}$ of the fluorescent dyes introduced into the specimen are usually known a priori or can be determined beforehand in a reference measurement. Here, for the sake of simplicity, they are grouped into a mixed matrix $M_{Det}$. The individual dye concentrations $c_i$ excited in the specimen upon measurement are the actual magnitudes sought (but not directly measurable) by the user. The individual dye concentrations $c_i$ can likewise be grouped mathematically into a concentration vector c. The detection side can, to this extent, be mathematically modeled, linking the energy states within the dye to the detection signals. If the excitation path is then considered, it is evident that the fluorescence generated by the dye, and thus the proportion of excited individual dye concentration $c_i$, once again depend on specific spectra $s_i^{ex}$ that determine the excitation of the dye population. The latter are once again known a priori or can be determined by reference measurement. The equation here is $$c = \sum_i I^{ex} s_i^{ex} = M_{Ex} I^{ex}; \qquad (2)$$

in other words, the excitation of an individual concentration is directly proportional to the portion of the excitation spectrum at the wavelength in the illumination light at which light is injected.

Figure 5:
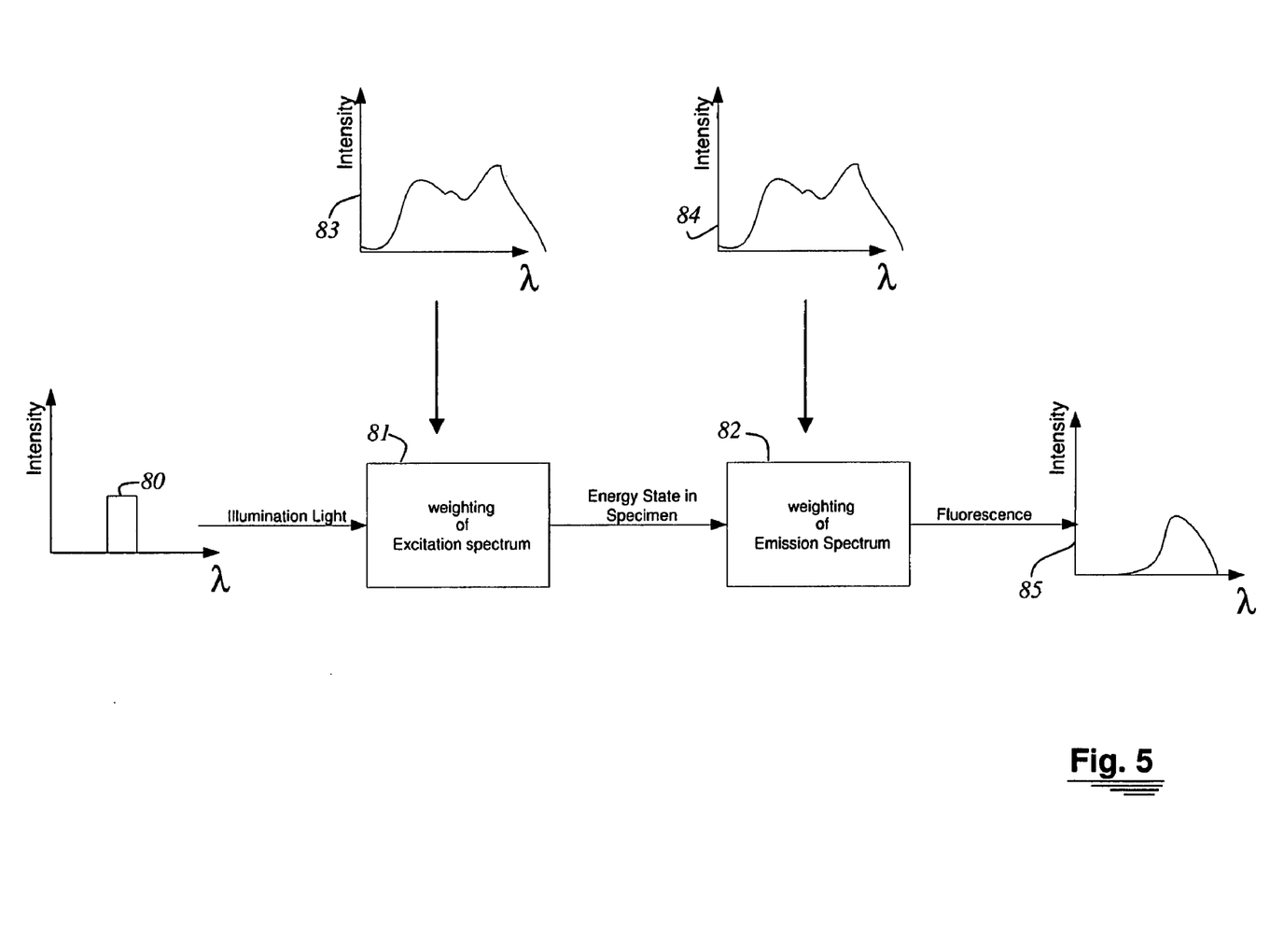
FIG. 5 is a graphical depiction of the processes in the spectral microscope and in the specimen.

This model of fluorescence image production is visualized in FIG. 5 and can be virtualized in computer system 23 using digital technology. Mathematically, it is a modeling operation in linear algebra. It is underdefined, i.e. there are multiple solutions that manifest themselves as a linear manifold in the overall space. This corresponds to the universally valid fact that there are several different system settings which yield images. For that reason, this modeling operation is also not used stringently in the existing art.

The system defined by equations (1) and (2) can, however, be used for the system configuration process. This is done by:

1. equipping the controlling computer system 23 with a database having spectral data for the various fluorescent dyes;

2. storing each spectrum in the database at least by name, emission spectrum, and absorption spectrum;

3. making that spectral database editable and expandable by the user;

4. making available in the user interface of the spectral microscope (more precisely in the controlling computer system 23, in embedded or added-on fashion) a selection means for at least one dye;

5. implementing the aforesaid model in the memory of computer system 23, by calculating the matrices $M_{Ex}$ and $M_{Det}$; and 6. accessing this data material in one of the following ways.

The manner in which this is done is the central concept of the invention, there being several alternatives. A number of trivial variants can be implemented. Matrices $M_{Ex}$ and $M_{Det}$ can be combined into a matrix $M=M_{Ex}M_{Det}$ with which further calculations can be performed. This variant describes the entire system as a kind of transfer function from illumination to detection. When modeling is to occur for a given illumination, the resulting spectra are generated directly by forward modeling. In the single-dye variant with one illumination, the resulting spectrum is obtained immediately as the result, and the configuration or setting of the mirror sliders of SP module 20 can be determined by a simple search. Matters become somewhat more difficult when two dyes are used with one illumination (e.g. GFP-CFP). Here the two spectral components are propagated individually through the matrix, and spectra are obtained that must be compared with one another in order to determine the setting of mirror stop arrangement 34, 35 of SP module 20. The goal is to shift sliders 40 and 41 to the point of greatest difference.

The reverse approach is also conceivable: for a given setting of mirror stop arrangement 34, 35, the optimum illumination is sought in order then to obtain optimum signals on detectors 36, 37 from the dyes present in specimen 15. This is done by calculating the pseudoinverses:

$$M^+ = \lim_{\alpha \to 0} (M^T M + \alpha I)^{-1} M^T$$

and projecting the regions of sliders 40 and 41 of mirror stop arrangement 34, 35 (in a vector representation) back into the illumination space. The closest illumination can then be selected there.

A feature common to all these embodiments, however, is the fact that they adhere to one individual case in order to work out a rough solution. In addition, they leave the effects in the dye out of consideration. The method disclosed here by the invention organizes the model in both directions. The matrices $M_{Ex}$ and $M_{Det}$ model the forward approach (the illumination is known, and a setting of mirror stop arrangement 34, 35 is applied in consideration of the dyes present in specimen 15), and the correspondingly associated pseudoinverses $M_{Ex}^+$ and $M_{Det}^+$ model the reverse approach (the setting of mirror stop arrangement 34, 35 is known, and a suitable illumination is selected in order to achieve optimum detection), the necessary data being derived from the database. In this fashion, all the relevant data about the configuration in specimen 15 ($I^{Det}$,c,$I^{Ex}$) can be directly combined with one another and reduced to the low-dimensional space of degrees of freedom ($I^{Ex}$). Proceeding from this possibility space, an optimum solution or setting of the system is sought. The configuration space must, however, be supplemented at a minimum with the detection characteristic of SP module 20 in the form of a projection matrix P, in order to model the grouping of spectral bands in SP module 20. An unmixing matrix U must additionally be introduced; it is used in computer system 23, following data acquisition, for data correction. The result is a configuration space to be searched, spanned by (U,P,$I^{Ex}$); the entire overdefined configuration space is in fact spanned by (U,P,$I^{Det}$,c,$I^{Ex}$), but the degrees of freedom are minimized by the aforementioned modeling. Evaluation and selection of a suitable configuration are generally accomplished by way of an optimization method and an evaluation function. Presentations of optimization methods are evident from the specialized mathematical literature (see, for example, Michaelewicz, Fogel, How to Solve It: Modern Heuristics. Berlin: Springer, 2000). It should be noted, however, that there are innumerable variants of optimization methods that are all, when suitably adapted, usable for this method.

An evaluation of the configuration could be accomplished, for example, under the following conditions, e.g.:
  $I^{Det}$ should be fairly bright;
  c should be as high as possible;
  $I^{Exc}$ should be as low as possible;
  the information in individual channels should be as different as possible;
  the total quantity of photons should be maximized;
  the risk of confusion should be minimized; or
  detection and internal excitation should be as identical as possible.

This can be implemented mathematically in very different ways. As a rule, it will result in an evaluation function such as $$\text{score} = -|I^{Exc}|\xi_1 + |c|\xi_2 + |I^{Det}|\xi_3 + \sum_i \sum_{i \neq j} -\log(I_i^{Det} - I_j^{Det})\xi_3 - |c - UPI^{Det}|\xi_4 + \ldots , \quad (3)$$

where the individual weightings $\xi_i$ produce comparability of scales. Each of the individual terms can have a meaning allocated to it, in this case illumination intensity, measured concentration, detection intensity, information difference between channels, concentration deviation of detected image, etc. An evaluation function of this kind can be correspondingly simplified to $$\text{score} = -|I_{Ex}|v + |M_{Ex}I_{Ex}|\zeta + |M_{Ex}M_{Det}I_{Ex}|\zeta + \ldots ,$$

which depends only on the illumination and can be maximized using an optimization algorithm.

FIG. 5 illustrates the mathematical and physical correlations in the context of the illumination and detection of a specimen 15 that is provided with fluorescent dyes. As already mentioned above, a specific spectral band 80 of illuminating light beam 4 is used to illuminate specimen 15. A thorough description has been given above of how, and under what preconditions, the selection is made. Together with excitation spectrum 83, a weighting 81 of spectral band 80 is performed. Energy states in specimen 15, and emission spectrum 84, are likewise subjected to a weighting 82. Ultimately a fluorescence spectrum 85 of specimen 15 is obtained.

Figure 6:
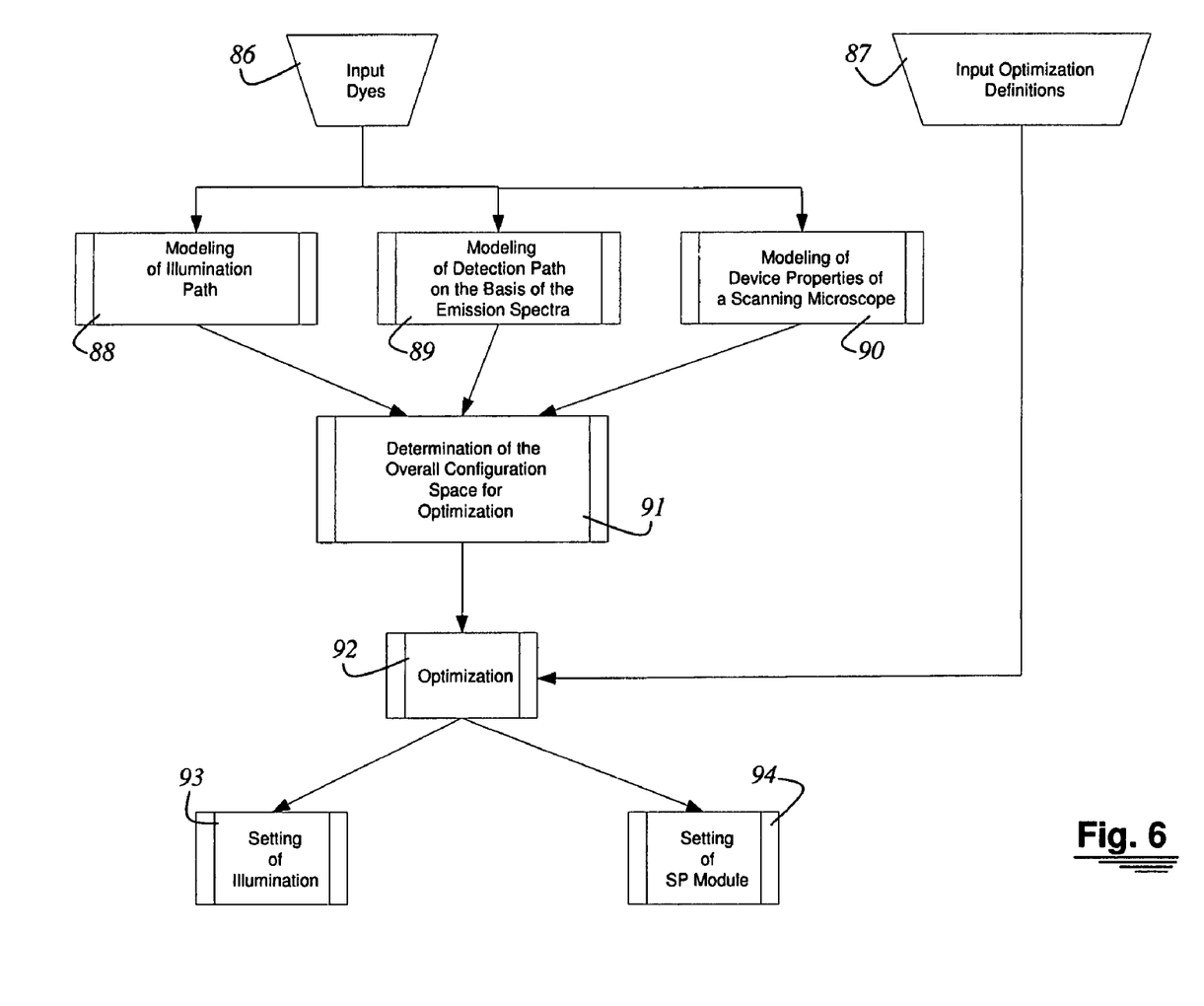
FIG. 6 is a graphical depiction of the method.

FIG. 6 is a schematic overview of the method according to the present invention. The first step is input 86 of the dyes with which specimen 15 is stained. The scanning microscope can derive the associated excitation and emission spectra from the database of computer system 23. The user can also, for example, make an input 87 of optimization definitions via peripheral device of spectral microscope 100. Based on the excitation and emission spectra retrieved from database 23a (FIG. 2) of computer system 23, a modeling 88 of the illumination path is performed on the basis of the excitation spectra. A modeling 89 of the detection path is also performed, on the basis of the emission spectra. A modeling 90 of the device properties of scanning microscope 100, which is embodied as a spectral microscope, is additionally accomplished. Based on the modeling 88, 89, 90 that has been performed, a determination 91 is made of the overall configuration space for optimization. An optimization 92 is then accomplished, in which input 87 of the optimization definitions is utilized. Optimization 92 results in a setting 93 of the illumination or light for fluorescence excitation. Optimization 92 also results in a setting 94 of SP module 20 in order to achieve optimum detection.

Figure 7:
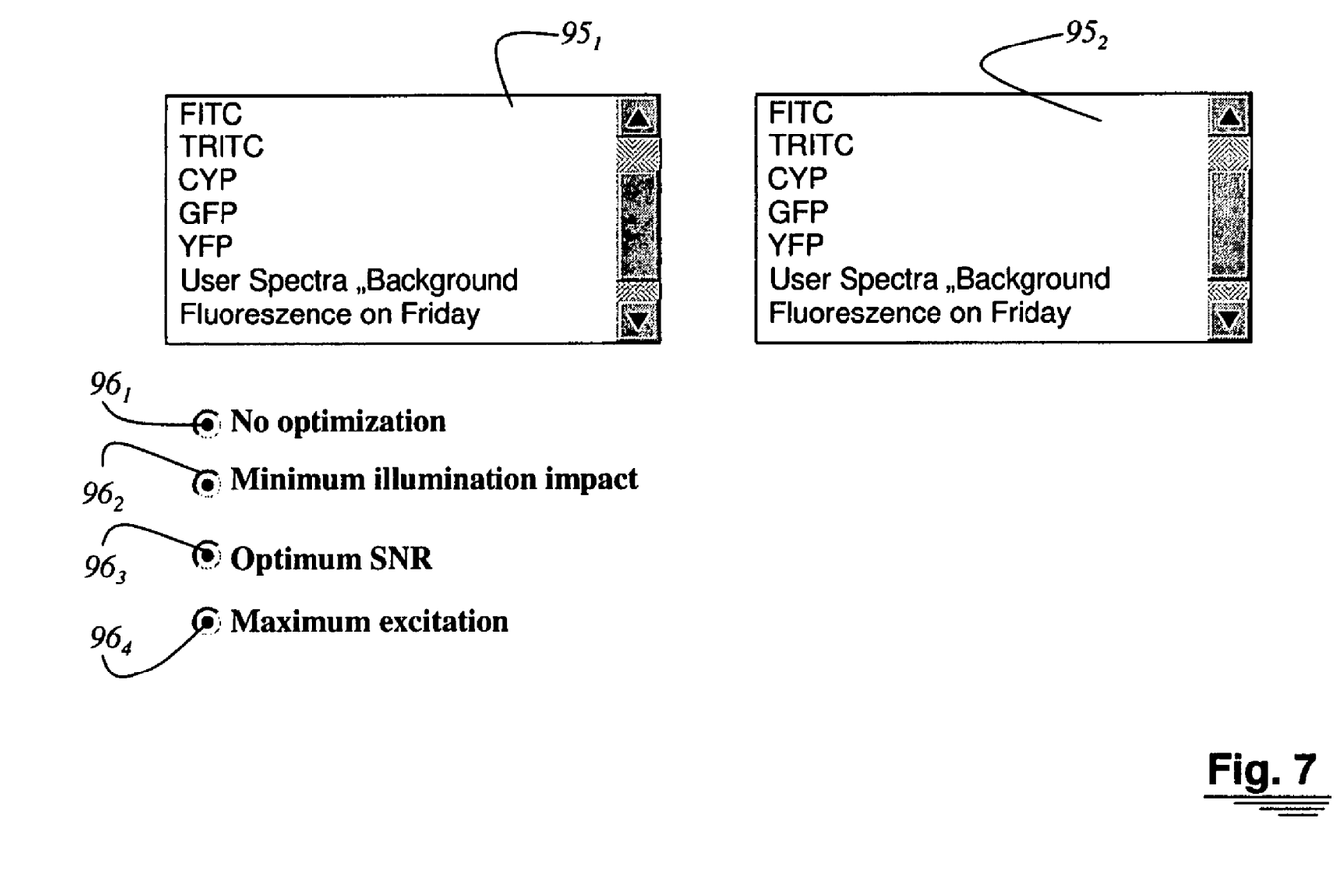
FIG. 7 shows the elements of a user interface for setting the system.

FIG. 7 shows an embodiment of a user interface having at least one selection means for dyes and a capability for selecting optimization goals. It is self-evident that the designations of the individual optimization goals are adapted to the needs of the market, and can in absolutely no way be construed as a limitation. All the other setting capabilities of a commercially available confocal microscope have been omitted for the sake of clarity. In a first and a second selection box $95_1$ and $95_2$, the user can select from a series of dyes provided in specimen 15. It is self-evident that more than two selection boxes can also be offered to the user. The number of selection boxes depends on the number of different dyes provided in specimen 15. In addition, the user is offered a plurality of checkboxes $96_1$, $96_2$, $96_3$, and $96_4$ for the activation of optimization goals. If the user activates, for example, first checkbox $96_1$ labeled "No optimization", he or she then does not wish to perform any optimization. If the user activates, for example, second checkbox $96_2$ labeled "Minimum illumination impact", he or she then wishes to minimize the illuminating light impact. If the user activates, for example, third clickbox $96_3$ labeled "Optimum SNR", the overall system will then be set in such a way as to obtain a good signal-to-noise ratio. If the user activates, for example, fourth clickbox $96_4$ labeled "Maximum excitation", the overall system will be then set so as to maximize the excitation of specimen 15 being investigated.

The invention has been described with reference to a particular embodiment. It is self-evident, however, that changes and modifications can be made without thereby leaving the range of protection of the claims below.

What is claimed is:

1. A method for determining illumination and detection parameters in a spectral scanning microscope for data acquisition comprising:
  generating light from at least one laser that emits light of one wavelength and converting the light of one wavelength into the light comprising a discrete or continuous wavelength region;
  calculating a band of the illuminating light for each fluorescent dye present in the specimen and calculating a band of a detected light for each fluorescent dye present in the specimen by using the excitation and emission spectra stored in a database;
  performing data acquisition with the spectral scanning microscope using for each fluorescent dye in the specimen its calculated band of the illuminating light within the wavelength region and its calculated band of a detected light,
  wherein the emission spectra $s_i^{em}$ of the fluorescent dyes in the specimen are grouped into a mixed detection matrix $M_{Det}$;
  wherein the excitation spectra $s_i^{ex}$ of the fluorescent dyes in the specimen are grouped into a mixed excitation matrix $M_{Ex}$;

wherein the mixed excitation matrix $M_{Ex}$ and the mixed detection matrix $M_{Det}$ model illumination conditions of the specimen, when a spectral composition of the illuminating light is known and a setting of a mirror stop arrangement is made in consideration of the fluorescent dyes present in the specimen.

2. The method as defined in claim 1, wherein the calculating step is performed automatically.

3. The method as defined in claim 1, wherein the specimen is provided with at least two fluorescent dyes.

4. The method as defined in claim 1, wherein calculation of the band of the illuminating light and of the detected band is accomplished by modeling and optimization of an optical configuration of the spectral scanning microscope in accordance with at least one boundary condition to be defined by the user.

5. The method as defined in claim 4, wherein the optical configuration of the spectral microscope takes into account an influence on the excitation spectrum and the emission spectrum of all optical elements of the spectral scanning microscope present in the illuminating light and in the detected light.

6. The method as defined in claim 4, wherein the boundary condition is an intensity of the illuminating light, a signal-to-noise ratio, a crosstalk ratio, or an erroneous detection risk.

7. The method as defined in claim 4, wherein the band of the illuminating light is set by means of an Acousto-Optical Beam Splitter.

8. The method as defined in claim 4, wherein the band of the detected light is set by means of a Spectral Photometer module.

9. The method as defined in claim 1, wherein calculation of the band of the illuminating light for each fluorescent dye present in the specimen, and calculation of the band of the detected light for each fluorescent dye present in the specimen, are preceded by an input of optimization definitions that the user performs via a peripheral device of the spectral scanning microscope.

10. The method as defined in claim 1, wherein upon detection, a spectral intensity vector $I^{Det}$, which is made up of a linear combination of the emission spectra $s_i^{em}$ of fluorescent dyes introduced into the specimen, is detected for each pixel of the specimen illuminated by the illuminating light.

11. The method as defined in claim 1, wherein for excitation, a spectral intensity vector $I^{Ex}$, which is made tip of a linear combination of the excitation spectra $s_i^{ex}$ of fluorescent dyes introduced into the specimen, is generated for each pixel of the specimen illuminated by the illuminating light.

12. A method for determining illumination and detection parameters in a spectral scanning microscope for data acquisition comprising:
generating light from at least one laser that emits light of one wavelength and converting the light of one wavelength into the light comprising a discrete or continuous wavelength region;
calculating a band of the illuminating light for each fluorescent dye present in the specimen and calculating a band of a detected light for each fluorescent dye present in the specimen by using the excitation and emission spectra stored in a database; and
performing data acquisition with the spectral scanning microscope using for each fluorescent dye in the specimen its calculated band of the illuminating light within the wavelength region and its calculated band of a detected light,
wherein the emission spectra $s_i^{em}$ of the fluorescent dyes in the specimen are grouped into a mixed detection matrix $M_{Det}$;
wherein the excitation spectra $s_i^{ex}$ of the fluorescent dyes in the specimen are grouped into a mixed excitation matrix $M_{Ex}$;
wherein a pseudoinverse $M_{Ex}^-$ of the mixed excitation matrix and a pseudoinverse $M_{Det}^-$ of the mixed detection matrix model detection conditions from the specimen to the detector, where a setting of a mirror stop arrangement is known and a suitable spectral composition of the illuminating light is selected.

13. The method as defined in claim 1, wherein the wavelength region is continuous and generated with a micro structured element or a tapered glass fiber.

14. A system for determining illumination and detection parameters in a fluorescence spectrum measurement system for microscopy, comprising:
a laser emitting light of one wavelength,
an illumination system that generates light of a continuous wavelength region from the light of one wavelength of the laser and defines illuminating light,
a Spectral Photometer module that receives a detected light proceeding from a specimen,
optical deflection means that is provided in the illuminating light and in the detected light,
a computer system with a database in which multiple excitation and emission spectra of each dye present in the specimen are stored:
means for calculating a spectral band of the illuminating light for each dye present in the specimen and for calculating a spectral band of the detected light for each dye present in the specimen, the means for calculating being implemented in the computer system comprising the excitation and emission spectra in the database of the computer system, means for determining illumination parameters from the calculated band in the illuminating light and means for determining the detection parameters from the calculated band in the detected light,
wherein the emission spectra $s_i^{em}$ of the dyes in the specimen are grouped into a mixed detection matrix $M_{Det}$;
wherein the excitation spectra $s_i^{ex}$ of the dyes in the specimen are grouped into a mixed excitation matrix $M_{Ex}$;
wherein the mixed excitation matrix $M_{Ex}$ and the mixed detection matrix $M_{Det}$ model illumination conditions of the specimen, when a spectral composition of the illuminating light is known and a setting of a mirror stop arrangement is made in consideration of the fluorescent dyes present in the specimen.

15. The system as defined in claim 14, wherein the means for determining illumination parameters from the calculated spectral band in the illuminating light is an optical deflection means.

16. The system as defined in claim 15, wherein the optical deflection means is an Acousto-Optical Beam Splitter.

17. The system as defined in claim 14, wherein the means for determining the detection parameters from the calculated band in the detected light is accomplished by an SP (Spectral Photometer) module.

18. The system as defined in claim 17, wherein the SP module comprises a mirror stop arrangement for selecting the calculated spectral band of the detected light in an emission spectrum.

19. The system as defined in claim 15, wherein the means for calculating comprises means for modeling and optimizing an optical configuration of the scanning microscope, a peripheral device for inputting at least one boundary condition.

20. The system as defined in claim 19, wherein the boundary condition is an intensity of the illuminating light, a signal-to-noise ratio, a crosstalk ratio, and/or an erroneous detection risk.

21. The system as defined in claim 19, wherein the peripheral device comprises a first and a second selection box for selecting several dyes in the specimen.

22. The system as defined in claim 21, wherein the peripheral device comprises a plurality of click boxes for activating optimization goals.

* * * * *